(12) United States Patent
Learmonth et al.

(10) Patent No.: US 9,206,135 B2
(45) Date of Patent: Dec. 8, 2015

(54) ASYMMETRIC CATALYTIC REDUCTION OF OXCARBAZEPINE

(71) Applicant: BIAL—Portela & C.A., S.A., S. Mamede do Coronado (PT)

(72) Inventors: David Alexander Learmonth, Alfena (PT); Gabriela Alexandra Grasa, Mantua, NJ (US); Antonio Zanotti-Gerosa, Cambridge (GB)

(73) Assignee: Bial-Portela & CA, S.A., S. Mamede do Coronado (PT)

( * ) Notice: Subject to any disclaimer, the term of this patent is extended or adjusted under 35 U.S.C. 154(b) by 0 days.

(21) Appl. No.: 13/651,844

(22) Filed: Oct. 15, 2012

(65) Prior Publication Data

US 2013/0041146 A1  Feb. 14, 2013

Related U.S. Application Data

(63) Continuation of application No. 11/997,104, which is a continuation of application No. PCT/GB2006/001473, filed on Apr. 21, 2006, now Pat. No. 8,288,532.

(30) Foreign Application Priority Data

Jul. 29, 2005 (GB) .................................. 0515690.6

(51) Int. Cl.
*A61K 31/55* (2006.01)
*C07D 223/22* (2006.01)

(52) U.S. Cl.
CPC ..................... *C07D 223/22* (2013.01)

(58) Field of Classification Search
CPC .............................. A61K 31/55; C07D 223/22
USPC .......................................... 540/589; 514/217
See application file for complete search history.

(56) References Cited

U.S. PATENT DOCUMENTS 5,753,646 A 5/1998 Benés et al.
7,189,846 B2 3/2007 Learmonth
(Continued)

FOREIGN PATENT DOCUMENTS

CA 2616984 A1 2/2007
CN 1566084 A 1/2005
(Continued)

OTHER PUBLICATIONS

Benes, Jan, et al., "Anticonvulsant and Sodium Channel-Blocking Properties of Novel 10,11-Dihydro-5H-dibenz[b,f] azepine-5-carboxamide Derivatives," J. Med. Chem., 1999, vol. 42, No. 14, pp. 2582-2587, American Chemical Society.

Bubert, Christian, et al., "Synthesis of water-soluble aminosulfonamide ligands and their application in enantioselective transfer hydrogenation," Tetrahedron Letters, 2001, vol. 42, pp. 4037-4039, Pergamon, Elsevier Science Ltd.

Deng, Jingen, et al., "Process for preparation of optically pure water-soluble 1,2-bis [2- (hydroxysulfonyl) phenyl] -1,2-ethylenediamine derivatives and application as asymmetric transfer hydrogenation catalysts," XP-002391168, 6 pages, CAPLUS, Oct. 2005.

Foreign communication from a related counterpart application—Decision to grant a European patent, EP 06726863.1, Jul. 21, 2011, 1 page.

(Continued)

*Primary Examiner* — Brenda Coleman
(74) *Attorney, Agent, or Firm* — Conley Rose, P.C.; Rodney B. Carroll

(57) ABSTRACT

A process for preparing (S)-(+)-10,11-dihydro-10-hydroxy-5H-dibenz/b,f/azepine-5-carboxamide or (R)-(−)-10,11-dihydro-10-hydroxy-5H-dibenz/b,f/azepine-5-carboxamide, by reduction of oxcarbazepine in the presence of a catalyst and a hydride source is disclosed. The catalyst is prepared from a combination of $[RuX_2(L)]_2$ wherein X is chlorine, bromine or iodine, and L is an aryl or aryl-aliphatic ligand, with a ligand of formula (A) or formula (B):

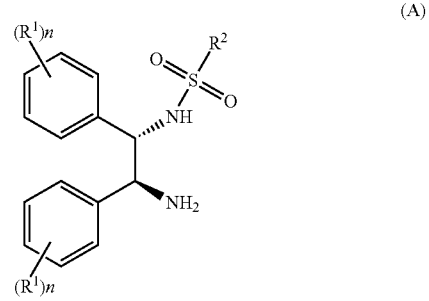

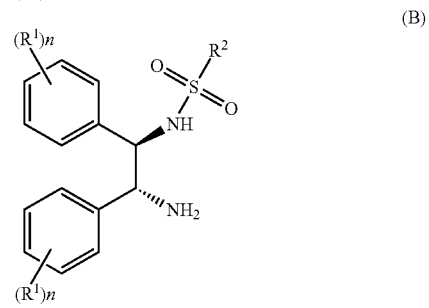

wherein $R^1$ is chosen from $C_{1-6}$ alkoxy and $C_{1-6}$ alkyl, n is a number from 0 to 5, and when n is a number from 2 to 5, $R^1$ can be the same or different, and $R^2$ is alkyl, substituted alkyl, aryl, substituted aryl, alkaryl or substituted alkaryl. The hydride source is either $NR^3R^4R^5$ and formic acid, $[R^3R^4R^5NH][OOCH]$ and optionally formic acid, or $[M][OOCH]_x$ and formic acid, wherein $R^3$, $R^4$ and $R^5$ are $C_{1-6}$ alkyl, M is an alkali metal or alkaline earth metal and x is 1 or 2. A pH from 6.5 to 8 is maintained during the process.

18 Claims, 1 Drawing Sheet

(56) References Cited

U.S. PATENT DOCUMENTS

| | | |
|---|---|---|
| 7,834,177 B2 | 11/2010 | Learmonth et al. |
| 7,999,100 B2 | 8/2011 | Learmonth et al. |
| 8,288,532 B2 | 10/2012 | Learmonth et al. |

FOREIGN PATENT DOCUMENTS

| | | |
|---|---|---|
| EP | 1308435 A2 | 5/2003 |
| EP | 1439159 A1 | 7/2004 |
| EP | 1512678 A1 | 3/2005 |
| EP | 0916637 B1 | 4/2005 |
| WO | 0076942 A1 | 12/2000 |
| WO | 02092572 A1 | 11/2002 |
| WO | 02096881 A1 | 12/2002 |
| WO | 2004031155 A1 | 4/2004 |
| WO | 2004099153 A1 | 11/2004 |
| WO | 2006005951 A1 | 1/2006 |
| WO | 2006075925 A2 | 7/2006 |
| WO | 2006075925 A3 | 7/2006 |
| WO | 2007012793 A1 | 2/2007 |

OTHER PUBLICATIONS

Foreign communication from a related counterpart application—International Preliminary Report on Patentability, PCT/GB2006/001473, Jan. 29, 2008, 6 pages.

Foreign communication from a related counterpart application—International Search Report and Written Opinion, PCT/GB2006/001473, Aug. 11, 2006, 9 pages.

Foreign communication from a related counterpart application—Japanese Office Action, Application No. 2008523428, Apr. 24, 2012, 3 pages.

Foreign communication from a related counterpart application—Response to Summons to Oral Proceedings, EP 06726863.1, Dec. 21, 2010, 29 pages.

"Guideline on the Specification Limits for Residues of Metal Catalysts or Metal Reagents," Committee for Medicinal Products for Human Use, European Medicines Agency, 2008, 3 pages, Annex 3 of Response.

Ma, Yaping, et al., "Asymmetric transfer hydrogenation of prochiral ketones in aqueous media with new water-soluble chiral vicinal diamine as ligand," XP-002326382, Organic Letters, 2003, pp. 2103-2106, vol. 5, No. 12, American Chemical Society.

Pharmaceutical Affairs Bureau Notification No. 307, "Guideline for Residual Solvents in Medicine." Mar. 30, 1998 (with partial translation), 16 pages (Reference 4 from Japanese Office Action, Application No. 2008523428).

Product brochures, "pH/ORP electrodes" and "pH electrodes," Mettler-Toledo, 11 pages, Annex 2 of Response, 2011.

Rhyoo, Hae Yoon, et al., "Use of surfactants in water-soluble ruthenium(II) complex-catalyzed asymmetric hydrogen-transfer reduction of aromatic ketones," Tetrahedron Letters, 2002, vol. 43, pp. 269-272, Pergamon, Elsevier Science Ltd.

VWR Laboratory Supplies Catalogue, "Apparatus, Instruments, Equipment & Consumables," 2007-2008, cover page and p. 662.47, Annex 1 of Response.

Wu, Xiaofeng, et al., "Insight into and practical application of pH-controlled asymmetric transfer hydrogenation of aromatic ketones in water," XP-002391156, Angew. Chem. Int. Ed., 2005, pp. 3407-3411, vol. 44, Wiley-VCH Verlag GmbH & Co. KGaA, Weinheim.

Xue, Dong, et al., "Transfer Hydrogenation of Activated C=C Bonds Catalyzed by Ruthenium Amido Complexes: Reaction Scope, Limitation, and Enantioselectivity," J. Org. Chem., 2005, vol. 70, No. 9, pp. 3584-3591, American Chemical Society.

Yamashita, Hiroshi, et al., "Practical synthesis of both enantiomers of vasopressin V2 receptor antagonist OPC-41061 using the catalytic asymmetric hydrogenation," Heterocycles, 2002, vol. 56, pp. 123-128.

Foreign communication from a related counterpart application—Examination Report, Canadian Patent Application No. 2,616,984, Apr. 2, 2014, 2 pages.

Foreign Communication—International Preliminary Report on Patentability of PCT/GB2004/001997 dated Nov. 18, 2005 (6 pages).

Foreign Communication—International Preliminary Report on Patentability of PCT/GB2005/002744 dated Jan. 16, 2007 (7 pages).

Foreign Communication—International Preliminary Report on Patentability of PCT/PT2006/000002 dated Jul. 17, 2007 (5 pages).

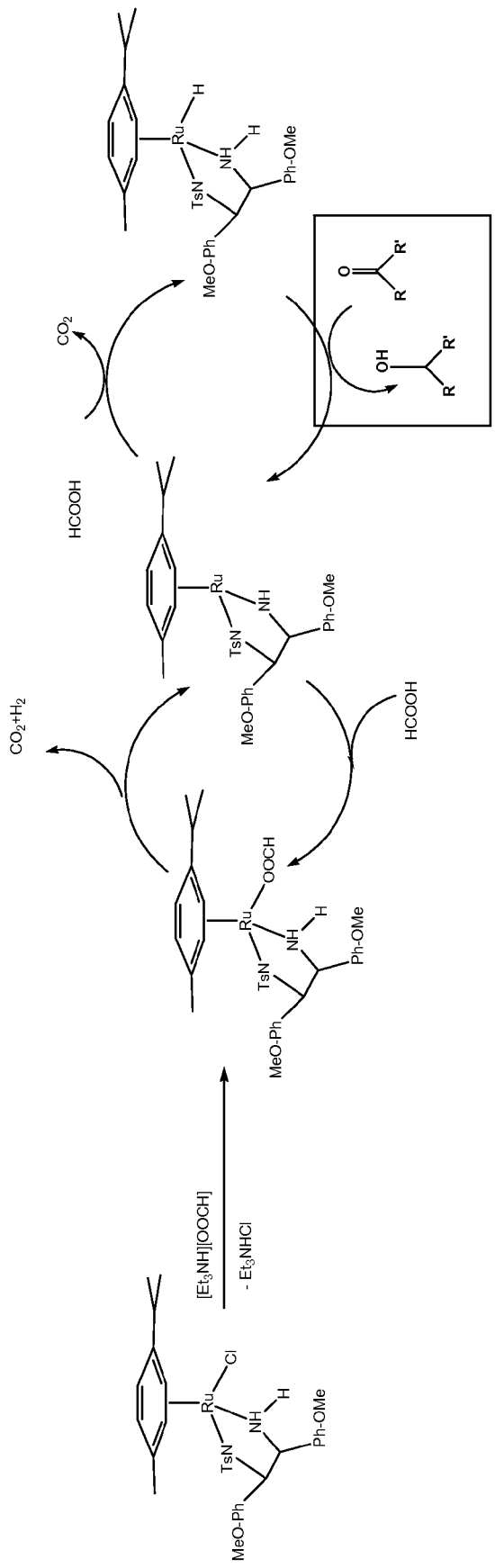

ASYMMETRIC CATALYTIC REDUCTION OF OXCARBAZEPINE

CROSS-REFERENCE TO RELATED APPLICATIONS

This application is a continuation of and claims priority to U.S. patent application Ser. No. 11/997,104 filed on Jun. 23, 2008 and published as U.S. Publication No. 2009/0203902A1, which is a filing under 35 U.S.C. 371 of International Application No. PCT/GB2006/001473 filed Apr. 21, 2006, entitled "Asymmetric Catalytic Reduction of Oxcarbazepine," claiming priority of Great Britain Patent Application No. GB 0515690.6 filed Jul. 29, 2005, which applications are incorporated by reference herein in their entirety.

FIELD OF THE INVENTION

The present invention relates to a process for the asymmetric catalytic reduction of oxcarbazepine(10,11-dihydro-10-oxo-5H-dibenz/b,f/azepine-5-carboxamide).

BACKGROUND OF THE INVENTION

Carbamazepine (I) and oxcarbazepine (II) are established first-line drugs used in the treatment of epilepsy:

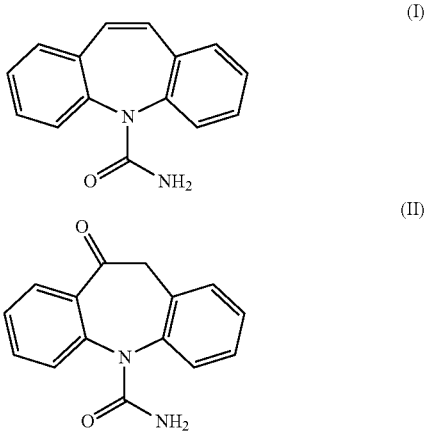

After oral administration to humans, oxcarbazepine (II) is rapidly metabolised to a pharmacologically active 4:1 mixture of the (S) and (R) enantiomers of 10,11-dihydro-10-hydroxy-5H-dibenz/b,f/azepine-5-carboxamide (III):

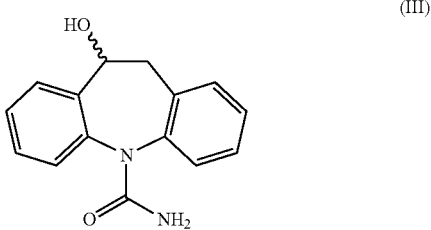 [SMILES: NC(=O)N1c2ccccc2CC(O)c2ccccc21]

WO02/096881 discloses a two-step process for the preparation of racemic (III) from carbamazepine. WO 02/092572 discloses a process for preparing a racemic mixture of (III) from oxcarbazepine and further discloses a process for resolving the (S) and (R)-enantiomers of (III) from the racemic mixture. The enantiomers can be used as intermediates in the preparation of (S)-(−)-10-acetoxy-10,11-dihydro-5H-dibenz/b,f/azepine-5-carboxamide and (R)-(+)-10-acetoxy-10,11-dihydro-5H-dibenz/b,f/azepine-5-carboxamide, two single-isomer drugs that may be used to treat epilepsy and other disorders of the central nervous system (Benes et al, U.S. Pat. No. 5,753,646).

WO 2004/031155 discloses a method for the enantioselective preparation of the (S) and (R)-enantiomers of (III) by asymmetric reduction of oxcarbazepine. The asymmetric reduction is carried out in the presence of a ruthenium catalyst and a hydride source. A suitable catalyst may be formed from $[RuCl_2(\text{p-cymene})]_2$ and (S,S)—N-(4-toluenesulfonyl)-diphenylethylenediamine (hereinafter referred to as (S,S)-TsDPEN). A mixture of formic acid and triethylamine (in a 5:2 molar ratio) is used as the hydride source. The disclosed process uses a very low substrate: catalyst ratio, i.e. a high amount of catalyst, (e.g. a ratio of 86:1 in example 1). The first major disadvantage of using such a high amount of catalyst is that the residual level of ruthenium metal, a most undesirable contaminant in the product, will be high and difficult to remove, and therefore the product will be unsuitable for use as an active pharmaceutical ingredient (API) or as a late-stage API intermediate. Regulatory guidance for residual metals derived from catalysts exists and the oral concentration limits for ruthenium residues are controlled particularly tightly. The second major disadvantage is that the ruthenium catalyst is expensive. The catalyst system described in WO 2004/031155 is very inefficient, and the cost contribution of the catalyst system alone prevents the process from being economically viable for large-scale manufacturing purposes.

The process disclosed in WO 2004/031155 also uses large quantities of the hydride source (7 equivalents of formic acid and 2.7 equivalents of triethylamine). Commercial sources of the formic acid/triethylamine mixture (triethylammonium formate) are available, but the mixture is expensive. The considerable excess of formic acid used in the process is potentially hazardous as the formic acid can decompose in the presence of the catalyst, causing gradual or spontaneous liberation of carbon dioxide and flammable hydrogen gas as well as causing pressure build-ups inside the reactor vessel. Premature degradation of the hydride source also means that the reduction reaction is slowed down considerably and does not reach full conversion even on prolonged reaction times, making the reaction even less efficient and ultimately providing product of low purity.

In the examples of WO 2004/031155 the crude product obtained by asymmetric reduction of oxcarbazepine is purified by column chromatography over silica gel. Purification by chromatography on scale is slow, expensive and in many cases impractical due to low throughput. The process disclosed in WO 2004/031155 is not suitable for use on a large scale in terms of efficiency and cannot be regarded as an industrially viable manufacturing process in terms of economy.

SUMMARY OF THE INVENTION

The present invention thus seeks to provide an improved method for the preparation of (S)-(+)-10,11-dihydro-10-hydroxy-5H-dibenz/b,f/azepine-5-carboxamide and (R)-(−)-10,11-dihydro-10-hydroxy-5H-dibenz/b,f/azepine-5-carboxamide, wherein the method is readily amenable to industrial batch-size production. Surprisingly, a process has been devised that can provide high yields of optically pure (S)-(+)-10,11-dihydro-10-hydroxy-5H-dibenz/b,f/azepine- 5-carboxamide and (R)-(−)-10,11-dihydro-10-hydroxy-5H-dibenz/b,f/azepine-5-carboxamide, using a greatly reduced quantity of catalyst (i.e. a high substrate/catalyst ratio).

Accordingly, the present invention provides a process for preparing (S)-(+)-10,11-dihydro-10-hydroxy-5H-dibenz/b,f/azepine-5-carboxamide or (R)-(−)-10,11-dihydro-10-hydroxy-5H-dibenz/b,f/azepine-5-carboxamide, by reduction of oxcarbazepine in the presence of a catalyst and a hydride source, wherein the catalyst is prepared from a combination of $[RuX_2(L)]_2$ wherein X is chlorine, bromine or iodine, and L is an aryl or aryl-aliphatic ligand, with a ligand of formula (A) or formula (B):

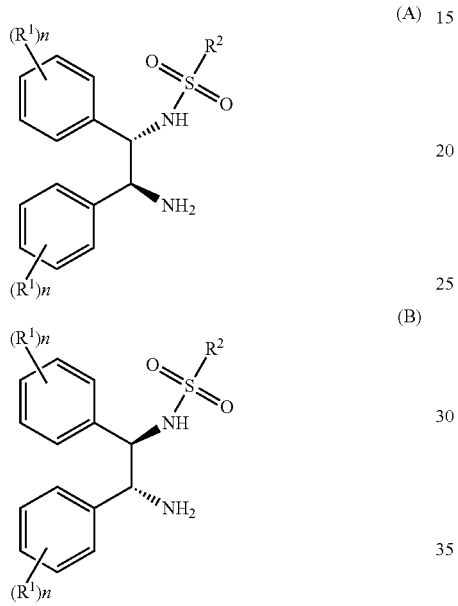

wherein $R^1$ is chosen from $C_{1-6}$ alkoxy and $C_{1-6}$ alkyl, n is a number from 0 to 5, and when n is a number from 2 to 5, $R^1$ can be the same or different, and $R^2$ is alkyl, substituted alkyl, aryl, substituted aryl, alkaryl or substituted alkaryl; wherein the hydride source is either $NR^3R^4R^5$ and formic acid, or $[R^3R^4R^5NH][OOCH]$ and optionally formic acid, or $[M][OOCH]_x$ and formic acid, wherein $R^3$, $R^4$ and $R^5$ are $C_{1-6}$ alkyl, M is an alkali metal or alkaline earth metal and x is 1 or 2, and wherein during the process a pH from 6.5 to 8 is maintained.

The present invention makes it possible to obtain optically pure (S)-(+)-10,11-dihydro-10-hydroxy-5H-dibenz/b,f/azepine-5-carboxamide or (R)-(−)-10,11-dihydro-10-hydroxy-5H-dibenz/b,f/azepine-5-carboxamide The expression "optically pure" is used to include compounds which have optical purity from 75-100%, preferably from 92-99.5%, more preferably from 96-99.5%.

BRIEF DESCRIPTION OF THE DRAWINGS

For a detailed description of the preferred embodiments of the disclosure, reference will now be made to the accompanying drawings in which:

FIG. 1 is an example of the catalytic cycle.

DETAILED DESCRIPTION OF THE INVENTION

The inventors have found that by controlling the pH of the reaction, it is now possible to achieve high isolated yields of optically pure (S)-(+)-10,11-dihydro-10-hydroxy-5H-dibenz/b,f/azepine-5-carboxamide or (R)-(−)-10,11-dihydro-10-hydroxy-5H-dibenz/b,f/azepine-5-carboxamide using acceptably small quantities of catalyst and of the hydride source reagents. The amount of residual ruthenium in the resulting product is very low, making it acceptable for use as an API intermediate. The process is now conveniently operable on a large-scale, and is economically viable, due to the lower cost contribution of the catalyst, simplified isolation procedure and improved yields.

The active catalyst is prepared from $[RuX_2(L)]_2$, and a ligand of formula (A) or formula (B):

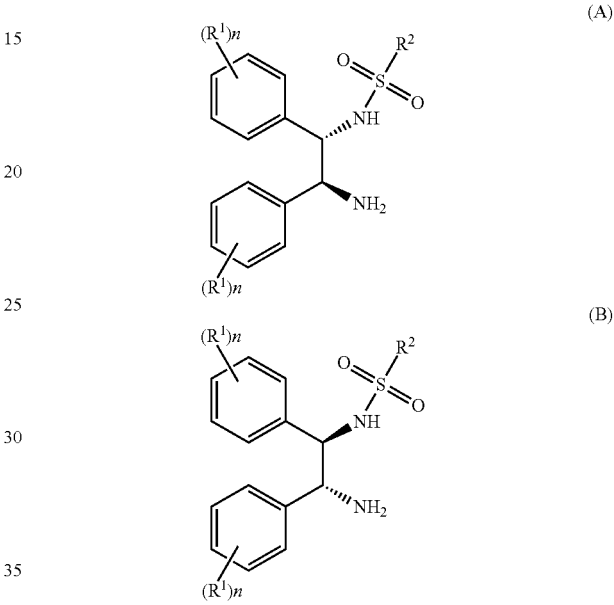

wherein X is chlorine, bromine or iodine, preferably chlorine; L is an aryl or aryl-aliphatic ligand such as p-cymene (isopropylmethylbenzene), benzene, hexamethylbenzene or mesitylene, and is preferably p-cymene. $R^1$ is chosen from $C_{1-6}$ alkoxy and $C_{1-6}$ alkyl, and n is a number from 0 to 5. When n is a number from 2 to 5, $R^1$ can be the same or different. Preferably, n is either 0 or 1 and when n is 1, $R^1$ is preferably either a methoxy or methyl group. Most preferably, $R^1$ is a methoxy group in the para position.

$R^2$ is an alkyl, substituted alkyl, aryl, substituted aryl, alkaryl or substituted alkaryl group, wherein the alkyl may be straight-chain, branched, cyclic or bridged and the alkyl, aryl or alkaryl groups may be substituted with alkyl, alkoxy, halogen or keto groups. When the $R^2$ group is an alkyl group, it may suitably contain 1 to 9 carbon atoms. When an alkyl group is substituted on the $R^2$ group, the alkyl group substituent may suitably contain 1 to 9 carbon atoms. The alkoxy or keto group substituent may suitably contain 1 to 9 carbon atoms. It is preferred that the alkoxy group substituent is methoxy.

Preferred $R^2$ groups are shown below:

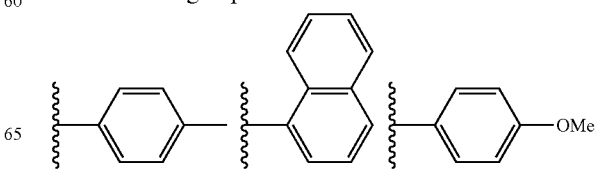

-continued

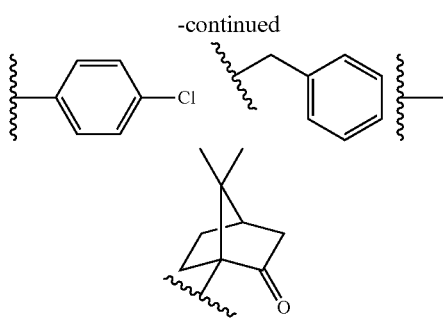

$R^2$ is preferably a phenyl group substituted by methyl, most preferably a phenyl group substituted by methyl at the para-position. Preferred ligands of formula (A) and (B) are shown below:

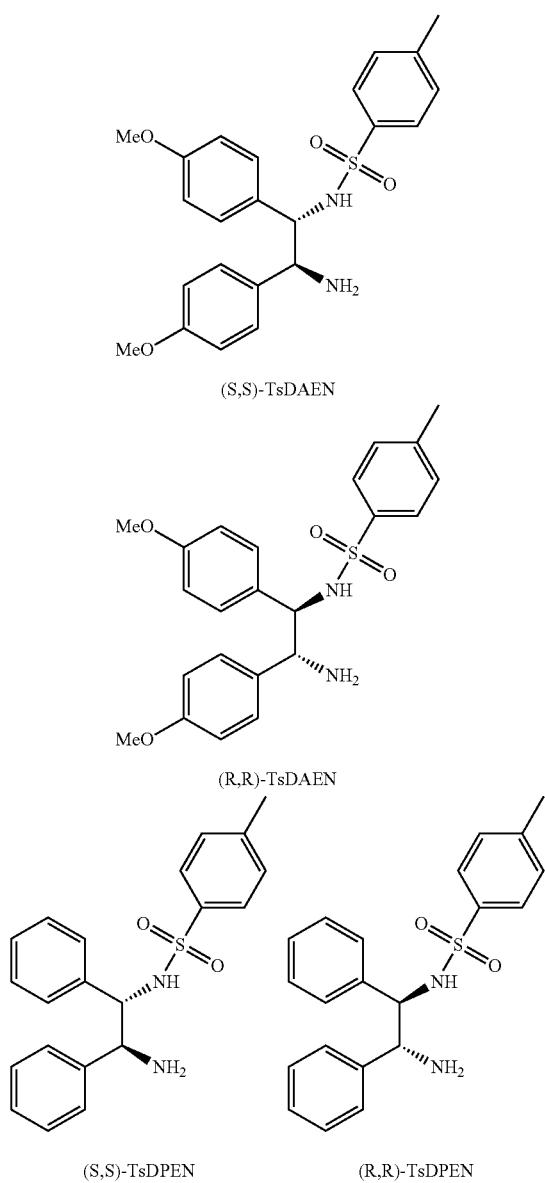

The most preferred ligands are (S,S)-TsDAEN and (R,R)-TsDAEN. It has been surprisingly discovered that substitution of the phenyl rings in particular by a methoxy substituent gives rise to a catalyst having greater efficiency for the asymmetric reduction of oxcarbazepine. Accordingly, much lower quantities of this catalyst are required for the preparation of (S) and (R)-10,11-dihydro-10-hydroxy-5H-dibenz/b,f/azepine-5-carboxamide from oxcarbazepine when compared to other ligands.

Processes using catalysts formed from ligands of formula (A) provide (S)-(+)-10,11-dihydro-10-hydroxy-5H-dibenz/b,f/azepine-5-carboxamide and processes using catalysts formed from ligands of formula (B) provide (R)-(−)-10,11-dihydro-10-hydroxy-5H-dibenz/b,f/azepine-5-carboxamide.

The catalyst is preferably prepared in situ, e.g. by combining $[RuX_2L]_2$ and the ligand of formula (A) or (B) under inert atmosphere in a solvent such as dimethylformamide (DMF). FIG. 1 provides an example of the catalytic cycle that is believed to take place (the hydride source in this example is $[Et_3NH][OOCH]$).

The molar ratio of oxcarbazepine to the ruthenium catalyst (which is equivalent to the molar ratio of oxcarbazepine to ruthenium) is suitably at least 500:1, preferably at least 1000:1, more preferably at least 1500:1. The process can been operated successfully at a molar ratio of oxcarbazepine to the ruthenium catalyst of 2700:1, therefore it is envisaged that the process can be operated with advantage, at oxcarbazepine to ruthenium catalyst ratios of at least 2000:1, more preferably at least 2500:1. It is expected that the process can be operated with oxcarbazepine to ruthenium catalyst ratios of at least 3000:1. Molar ratios lower than 500:1 are not preferred because the precious metal catalyst is expensive and may result in unacceptably high residual ruthenium levels in the isolated product. The process of the invention wherein the pH of the reaction mixture is controlled allows for a significantly improved substrate:catalyst ratios compared to prior art methods wherein the pH is not controlled, e.g. example 1 process of WO 2004/031155 uses an oxcarbazepine to ruthenium ratio of 86:1.

The hydride source is either $NR^3R^4R^5$ and formic acid, or $[R^3R^4R^5NH][OOCH]$ and optionally formic acid, or $[M][OOCH]_x$ and formic acid, wherein $R^3$, $R^4$ and $R^5$ are $C_{1-6}$ alkyl, M is an alkali metal or alkaline earth metal and x is 1 or 2. $R^3$, $R^4$ and $R^5$ may be the same or different, but are preferably all the same. The $C_{1-6}$ alkyl groups may be straight-chain, branched or cyclic. Preferably $R^3$, $R^4$ and $R^5$ are ethyl, propyl or butyl, most preferably ethyl. M is preferably Na, Li or K, most preferably Na. When M is an alkali metal x is 1 and when M is an alkaline earth metal, x is 2.

$[R^3R^4R^5NH][OOCH]$ reagents, e.g. $[Et_3NH][OOCH]$, are commercially available. $[Et_3NH][OOCH]$ is commonly used in asymmetric reduction reactions but is synthesised from $H_2$, $CO_2$ and $NEt_3$ in the presence of a ruthenium catalyst and is therefore expensive, so it is desirable to minimise the use of this type of reagent. When formic acid and $NR^3R^4R^5$ are mixed in a stoichiometric amount, the following acid base equilibrium occurs:

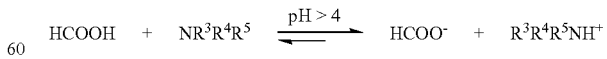

At low pH, the hydride source exists in its acid form, while at higher pH, it exists in its conjugate base form, a species that participates in the catalytic cycle.

In a first embodiment of the invention, the hydride source is $NR^3R^4R^5$ and formic acid, preferably triethylamine and formic acid. This embodiment avoids the use of the expensive

[R³R⁴R⁵NH][OOCH] reagents. Suitably, the NR³R⁴R⁵ is added to the reaction mixture at the start of the process. Preferably less than two equivalents of NR³R⁴R⁵ are added, most preferably about one equivalent. The amount of formic acid that is added to the reaction mixture at the start of the process can be minimised. This is advantageous because the formic acid decomposes to carbon monoxide and hydrogen during the process, and this is potentially hazardous if large quantities of formic acid are used. Suitably less than 1.5 equivalents of formic acid are added to the reaction mixture at the start of the process, preferably less than 1 equivalent, most preferably less than 0.2 equivalents. If less than 1 equivalent of formic acid is added at the start of the process, further formic acid should be added during the course of the reaction, providing about 1-3 equivalents of formic acid in total.

In a second embodiment of the invention, the hydride source is [R³R⁴R⁵NH][OOCH], preferably [Et₃NH][OOCH], with or without formic acid. Suitably the [R³R⁴R⁵NH][OOCH] is added to the reaction mixture at the start of the process. Preferably less than two equivalents of [R³R⁴R⁵NH][OOCH] are used, preferably about one equivalent. Suitably less than 0.5 equivalents of formic acid are added to the reaction mixture at the start of the process, most preferably less than 0.2 equivalents. Further formic acid may be added to the reaction mixture during the course of the reaction.

In a third embodiment of the invention, the hydride source is [M][OOCH]$_x$, preferably NaOOCH, and formic acid. Suitably the [M][OOCH]$_x$ is added to the reaction mixture at the start of the process. Preferably less than two equivalents of [M][OOCH]$_x$ are used, preferably about one equivalent. Suitably less than 1.5 equivalents of formic acid are added to the reaction mixture at the start of the process, preferably less than 1 equivalent, most preferably less than 0.2 equivalents. If less than 1 equivalent of formic acid is added at the start of the process, further formic acid should be added during the course of the reaction, providing about 1-3 equivalents of formic acid in total.

The process of the invention allows for reduced quantities of hydride source reagents than prior art methods, e.g. the process of WO 2004/031155 wherein pH is not controlled uses seven equivalents of formic acid and 2.7 equivalents of triethylamine. In particular, the process of the present invention minimises the hazards associated with adding large quantities of formic acid to the reaction mixture at the start of the reaction.

The pH of the reaction mixture is maintained between 6.5 and 8 during the course of the reaction. Control of pH is essential to provide good conversions and acceptably high product yields, preferably above 85%, whilst using acceptably low quantities of catalyst (e.g. a substrate: catalyst ratio of 500 or more). The pH can be monitored by methods known to those skilled in the art, but a preferred method is to use a Hamilton gel-filled electrode as described in the Examples of the present invention.

The preferred method of controlling the pH is to add formic acid in a controlled manner during the course of the reaction, e.g. by titration. Most preferably, the pH is maintained from 7.0 to 7.8 by the controlled addition of formic acid. In the first embodiment of the invention, wherein the hydride source is NR³R⁴R⁵ and formic acid, up to 1.5 equivalents of formic acid may be added at the start of the process and then further formic acid may be added as necessary to maintain the pH. However, it is preferred that no formic acid is added to the reaction mixture when the NR³R⁴R⁵ is added, and all the formic acid is added in a gradual, controlled manner, e.g. dropwise by titration, thus maintaining the pH from 6.5 to 8.

It is preferred to add all the formic acid in a gradual, controlled manner because this minimises the hazards associated with decomposition of formic acid. In the second embodiment of the invention, wherein the hydride source comprises [R³R⁴R⁵NH][OOCH], it is preferred that no formic acid is added at the start of the process but that formic acid is subsequently added to maintain the pH. The formic acid is suitably added in a gradual, controlled manner, e.g. dropwise by titration, thus maintaining the pH from 6.5 to 8. In the third embodiment of the invention, wherein the hydride source is [M][OOCH]$_x$ and formic acid, up to 1.5 equivalents of formic acid may be added at the start of the process and then further formic acid may be added as necessary to maintain the pH. However, it is preferred that no formic acid is added to the reaction mixture when the [M][OOCH]$_x$ is added, and all the formic acid is added in a gradual, controlled manner, e.g. dropwise by titration, thus maintaining the pH from 6.5 to 8.

The solubility of oxcarbazepine is appreciably low in most pharmaceutically acceptable process solvents, even at elevated temperatures. Suitable solvents may comprise dimethylformamide (DMF), ethyl acetate (EtOAc), acetonitrile, isopropyl acetate, tetrahydrofuran, 1,2-dichloroethane, dimethoxy ethane and/or water. It is preferred that the solvent comprises at least one polar aprotic solvent such as DMF or acetonitrile because these solvents are miscible with both organic and inorganic phases. Surprisingly, standard non-deoxygenated reagent grade solvents are suitable for use in the process of the present invention. A preferred solvent system for the process of the present invention is a mixture of two or more solvents selected from DMF, EtOAc, acetonitrile and water. In the first embodiment of the invention wherein the hydride source is NR³R⁴R⁵ and formic acid, the solvent suitably comprises 0-25% DMF, 0-25% water and 75-95% EtOAc or 0-25% acetonitrile, 0-25% water and 75-95% EtOAc, preferably 0-20% DMF, 5-20% water and 80-90% EtOAc. The most preferred solvent is 10% DMF, 10% water and 80% EtOAc. In the second embodiment of the invention wherein the hydride source is [R³R⁴R⁵NH][OOCH] with or without formic acid, the solvent suitably comprises 5-25% DMF and 75-95% EtOAc, 5-25% acetonitrile and 75-95% EtOAc, 5-25% DMF and 75-95% water, or 5-25% acetonitrile and 75-95% water. In the third embodiment of the invention, wherein the hydride source is [M][OOCH]$_x$ and formic acid the solvent suitably comprises 0-25% DMF, 0-25% water and 75-95% EtOAc or 0-25% acetonitrile, 0-25% water and 75-95% EtOAc, preferably 0-20% DMF, 5-20% water and 80-90% EtOAc.

In a particular embodiment of the process, the reduction takes place in the presence of a phase transfer catalyst. Suitable phase transfer catalysts include quaternary alkyl ammonium halides, such as for example Bu₄NBr. The ratio of phase transfer catalyst to catalyst is suitably from 0.01 to 0.5, preferably about 0.1.

The reaction can be carried out at different temperatures and pressures. Suitably the reaction is carried out at atmospheric pressure and at the reflux temperature of the preferred solvent system. An external temperature of 100-120° C., more preferably 105-110° C. is appropriate for the most preferred solvent systems.

The reaction time will depend on key factors such as the ratio of oxcarbazepine to catalyst. Preferably the reaction should be completed in less than 36 hours, more preferably in less than 24 hours and high yields have been achieved by applying the process of the present invention in reaction times of less than 24 hours at oxcarbazepine to catalyst ratios even greater than 2000:1.

In the first embodiment of the invention wherein the hydride source is NR³R⁴R⁵ and formic acid, the product may spontaneously precipitate from the reaction mixture as it cools from reflux temperature. A suitable solvent, preferably methyl tert-butyl ether (MTBE) is added to the reaction mixture before filtration. In the second embodiment of the invention wherein the hydride source is [R³R⁴R⁵NH][OOCH] with or without formic acid, the product may be isolated by precipitating the crude product from suitable solvent mixtures, preferably either methanol/water or methanol/MTBE at 0-5° C. The work-up procedures are particularly simple compared to prior art methods such as those disclosed in WO 2004/031155 wherein the work-up procedure requires neutralisation of excess formic acid, extraction, drying, solvent evaporation and flash chromatography. These procedures are unsuitable for large-scale manufacture. In the present invention the simple work-up procedures result in acceptably low residual ruthenium content in the isolated product, consistent with its intended use as a final intermediate in the manufacture of APIs.

In an alternative embodiment, the (S)-(+)-10,11-dihydro-10-hydroxy-5H-dibenz/b,f/azepine-5-carboxamide or (R)-(−)-10,11-dihydro-10-hydroxy-5H-dibenz/b,f/azepine-5-carboxamide may be precipitated by removing the reaction solvent while adding water to maintain the reaction volume at a substantially constant level. The reaction solvent, which is preferably ethyl acetate, may be removed by distillation. The distillation temperature is preferably at least 60° C. Typically the weight of water replacing the reaction solvent may be in the range 80-120%, more preferably 90-110% of the weight of the solvent removed. In this embodiment, the removal of the precipitated (S)-(+)-10,11-dihydro-10-hydroxy-5H-dibenz/b,f/azepine-5-carboxamide or (R)-(−)-10,11-dihydro-10-hydroxy-5H-dibenz/b,f/azepine-5-carboxamide may subsequently be isolated by filtration, and can be further purified, preferably by reslurrying in a solvent, which is preferably ethyl acetate and re-filtration.

Another advantage of the present invention is that it is possible to run the reaction with a high substrate concentration e.g. 0.5-1.5M, so that the volume efficiency of the reaction is very good. This is especially relevant when considering large-scale manufacturing.

The (S)-(+)-10,11-dihydro-10-hydroxy-5H-dibenz/b,f/azepine-5-carboxamide or (R)-(−)-10,11-dihydro-10-hydroxy-5H-dibenz/b,f/azepine-5-carboxamide produced according to the process of the present invention may be used as an API and formulated into finished pharmaceutical products, or may be converted by further chemical transformation to another API, e.g. (S)-(−)-10-acetoxy-10,11-dihydro-5H-dibenz/b,f/azepine-5-carboxamide may be provided by esterification of (S)-(+)-10,11-dihydro-10-hydroxy-5H-dibenz/b,f/azepine-5-carboxamide. The present invention further provides a process for preparing a compound of formula (C) or (D)

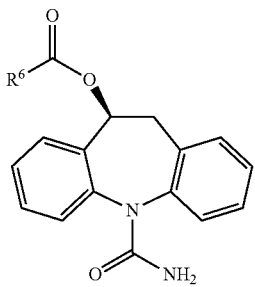

(C)

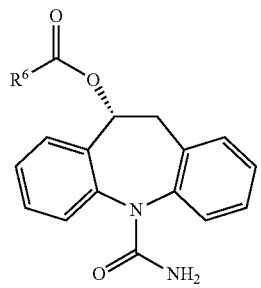

(D)

wherein R⁶ is hydrogen, alkyl, halogenalkyl, aralkyl, cycloalkyl, cycloalkyalkyl, alkoxy, aryl or pyridyl; comprising a first step, which is a process for the production of (S)-(+)-10,11-dihydro-10-hydroxy-5H-dibenz/b,f/azepine-5-carboxamide or (R)-(−)-10,11-dihydro-10-hydroxy-5H-dibenz/b,f/azepine-5-carboxamide according to the invention, and a second step, wherein the (S)-(+)-10,11-dihydro-10-hydroxy-5H-dibenz/b,f/azepine-5-carboxamide or (R)-(−)-10,11-dihydro-10-hydroxy-5H-dibenz/b,f/azepine-5-carboxamide is acylated. The compounds produced in accordance with this process may be optically pure, wherein optically pure means compounds which have optical purity from 75-100%, preferably from 92-99.5%, more preferably from 96-99.5%.

R⁶ may be straight or branched $C_{1-18}$ alkyl, which may be substituted with halogen (F, Cl, Br or I). It may also be cycloalkyl (a cyclic $C_3$-$C_6$ saturated group) or aryl (unsubstituted phenyl or phenyl substituted by alkoxy, halogen or nitro group). Preferably R⁶ is CH₃. Compounds of formula (C) and (D) are further described in U.S. Pat. No. 5,753,646. Suitable acylation methods are described in U.S. Pat. No. 5,753,646 and WO 02/092572, e.g. (S)-(+)-10,11-dihydro-10-hydroxy-5H-dibenz/b,f/azepine-5-carboxamide may be reacted with acetylchloride or acetic anhydride in dichloromethane to give (S)-(−)-10-acetoxy-10,11-dihydro-5H-dibenz/b,f/azepine-5-carboxamide.

The appropriate stereoisomers of the following additional compounds may also be converted from (S)-(+)-10,11-dihydro-10-hydroxy-5H-dibenz/b,f/azepine-5-carboxamide or (R)-(−)-10,11-dihydro-10-hydroxy-5H-dibenz/b,f/azepine-5-carboxamide using an appropriate process, as described in U.S. Pat. No. 5,753,646:

(1) 10-benzoyloxy-10,11-dihydro-5H-dibenz/b,f/azepine-5-carboxamide
(2) 10-(4-methoxybenzoyloxy)-10,11-dihydro-5H-dibenz/b,f/azepine-5-carboxamide
(3) 10-(3-methoxybenzoyloxy)-10,11-dihydro-5H-dibenz/b,f/azepine-5-carboxamide
(4) 10-(2-methoxybenzoloxy)-10,11-dihydro-5H-dibenz/b,f/azepine-5-carboxamide
(5) 10-(4-nitrobenzoyloxy)-10,11-dihydro-5H-dibenz/b,f/azepine-5-carboxamide
(6) 10-(3-nitrobenzoyloxy)-10,11-dihydro-5H-dibenz/b,f/azepine-5-carboxamide
(7) 10-(2-nitrobenzoyloxy)-10,11-dihydro-5H-dibenz/b,f/azepine-5-carboxamide
(8) 10-(4-chlorobenzoyloxy)-10,11-dihydro-5H-dibenz/b,f/azepine-5-carboxamide
(9) 10-(3-chlorobenzoyloxy)-10,11-dihydro-5H-dibenz/b,f/azepine-5-carboxamide
(10) 10-(2-acetoxybenzoyloxy)-10,11-dihydro-5H-dibenz/b,f/azepine-5-carboxamide

(11) 10-propionyloxy-10,11-dihydro-5H-dibenz/b,f/azepine-5-carboxamide
(12) 10-butyryloxy-10,1-dihydro-5H-dibenz/b,f/azepine-5-carboxamide
(13) 10-pivaloyloxy-10,11-dihydro-5H-dibenz/b,f/azepine-5-carboxamide
(14) 10-[(2-propyl)pentanoyloxy]-10,11-dihydro-5H-dibenz/b,f/azepine-5-carboxamide
(15) 10-[(2-ethyl)hexanoyloxy]-10,11-dihydro-5H-dibenz/b,f/azepine-5-carboxamide
(16) 10-stearoyloxy-10,11-dihydro-5H-dibenz/b,f/azepine-5-carboxamide
(17) 10-cyclopentanoyloxy-10,11-dihydro-5H-dibenz/b,f/azepine-5-carboxamide
(18) 10-cyclohexanoyloxy-10,11-dihydro-5H-dibenz/b,f/azepine-5-carboxamide
(19) 10-phenylacetoxy-10,11-dihydro-5H-bibenz/b,f/azepine-5-carboxamide
(20) 10-(4-methoxyphenyl)acetoxy-10,11-dihydro-5H-dibenz/b,f/-azepine-5-carboxamide
(21) 10-(3-methoxyphenyl)acetoxy-10,11-dihydro-5H-dibenz/b,f/azepine-5-carboxamide
(22) 10-(4-nitrophenyl)acetoxy-10,11-dihydro-5H-dibenz/b,f/azepine-5-carboxamide
(23) 10-(3-nitrophenyl)acetoxy-10,11-dihydro-5H-dibenz/b,f/azepine-5-carboxamide
(24) 10-nicotinoyloxy-10,11-dihydro-5H-dibenz/b,f/azepine-5-carboxamide
(25) 10-isonicotinoyloxy-10,11-dihydro-5H-dibenz/b,f/azepine-5-carboxamide
(26) 10-chloroacetoxy-10,11-dihydro-5H-dibenz/b,f/azepine-5-carboxamide
(27) 10-bromoacetoxy-10,11-dihydro-5H-dibenz/b,f/azepine-5-carboxamide
(28) 10-formyloxy-10,11-dihydro-5H-dibenz/b,f/azepine-5-carboxamide
(29) 10-ethoxycarbonyloxy-10,11-dihydro-5H-dibenz/b,f/azepine-5-carboxamide
(30) 10-(2-chloropropionyloxy-10,11-dihydro-5H-dibenz/b,f/azepine-5-carboxamide The invention is now described by reference to examples, which are not intended to be limiting thereof.

EXAMPLES

Example 1

Asymmetric Reduction of Oxcarbazepine Using $NEt_3$ and pH-Controlled Addition of HCOOH In a 2 L 5-necked round bottom flask, oxcarbazepine was charged (635 mmol, 169 g), the flask was fitted with two water reflux condensers connected to a Schlenk line (two reflux condensers were used to secure two escape routes for $CO_2$ and $H_2$ gases evolving from the reaction), a burette for titration and a Hamilton gel-filled electrode fitted through a hollow GL25 screw cap equipped with a PTFE/silicone ring. To the starting material under $N_2$ flow, EtOAc (480 mL, undegassed, HPLC grade), $H_2O$ (48 mL, undegassed, HPLC grade) and $Et_3N$ (1.1 eq., 699 mmol, 97.5 mL, undegassed, Fluka, 99.9% pure) were added with the aid of a graduated cylinder. The catalyst (formed separately in situ in a 50 mL Schlenk tube under $N_2$ flow by stirring $[RuCl_2(p\text{-cymene})]_2$ (0.1588 mmol, 97.2 mg) and (S,S)-TsDAEN (2.2 eq. with respect to the metal dimer precursor, 0.3493 mmol, 159 mg) in DMF (13 mL, degassed, anhydrous) at room temperature for 10-15 min. was injected. The Schlenk tube was rinsed with small portions of the remaining DMF (5×7 mL) and injected to the reaction mixture. The solvent combination at this point was 10% DMF-10% $H_2O$-80% EtOAc (v/v/v) and the substrate concentration before titration was 1.1M. The round bottom flask was placed in an oil bath preheated at 105° C. and the reaction mixture magnetically stirred at reflux ($T_{oil\ bath}$=105° C., internal T=72-77° C.). Once the reaction mixture started refluxing, the reaction pH was approximately 8.8. At this point the titration/slow addition with 12.5 M HCOOH solution in 20% DMF/EtOAc was started. The pH was slowly brought to 7.4 and then maintained constant at this value over 12 hrs by slowly adding the HCOOH solution. The HPLC conversion after 15 hrs was 99%. Further stirring up to 20 hrs resulted in the formation of a white precipitate and has not consumed the remaining 1% oxcarbazepine. A total of approximately 3.7 eq. HCOOH with respect to the starting material was consumed during the reaction. The overall substrate/product concentration at the end of the reaction was 0.86 M. After 20 hrs, the heating was stopped and the reaction mixture was stirred and allowed to cool down slowly. When the temperature of the oil bath reached approximately 80° C., 500 mL MTBE was added to the reaction mixture and allowed to cool to room temperature under stirring. The reaction mixture was stirred at 0-5° C. for approximately 30 min, filtered and the precipitate was washed repeatedly with cold portions of MTBE until the filtrate was colourless. The resulting white precipitate was dried in the air, then under high vacuum, affording a white powder: 95% isolated yield (152 g). HPLC: 99.6% product, 97.8% e.e., 0.4% oxcarbazepine.

Due to the fact that under these reaction conditions (10% DMF-10% $H_2O$-80% EtOAc, 1.1 eq. $Et_3N$ and HCOOH) the product crystallises out at the refluxing temperature, no solvent was evaporated during the work-up. The very low solubility of the product in MTBE, allows not only further precipitation of the starting material, but also it aids the purification/removal of residual ruthenium, DMF and reagents by washing the filtrate with copious amounts, without a loss in the isolated yield. The ruthenium level in the product was between 5-50 ppm.

Example 2

Asymmetric Reduction of Oxcarbazepine Using $[Et_3NH][OOCH]$ and pH-Controlled Addition of HCOOH In a 500 mL 4-necked round bottom flask, oxcarbazepine was charged (159 mmol, 40 g), the flask fitted with a water reflux condenser connected to a Schlenk line, a burette for titration and a Hamilton gel filled electrode fitted through a hollow GL25 screw cap with a PTFE/silicone ring. The flask was flushed with $N_2$ for approximately 30 min. To the starting material under $N_2$ flow, EtOAc (78 mL, degassed, anhydrous), $[Et_3NH][OOCH]$ commercially available from Fluka (1.07 eq., 170 mmol, 25 mL, undegassed, Fluka) were added via a syringe. The catalyst (formed separately in situ in a 20 mL Schlenk tube by stirring $[RuCl_2(p\text{-cymene})]_2$ (0.0265 mmol, 16.2 mg) and (S,S)-TsDAEN (2.2 eq. with respect to the metal dimer precursor, 0.0582 mmol, 25 mg) in DMF (5 mL, degassed, anhydrous) at room temperature for 10-15 min. was injected. The Schlenk tube was rinsed with small portions of the remaining DMF (5×3 mL) and injected to the reaction mixture. The solvent combination at this point was 20% DMF-80% EtOAc (v/v) and the oxcarbazepine concentration before titration was 1.3M. The round bottom flask was placed in an oil bath preheated at 105° C. and the reaction mixture was magnetically stirred at reflux ($T_{oil\ bath}$=105° C.).

Once the reaction mixture started refluxing, the reaction pH was approximately 6.8. The reaction mixture slowly turned purple and the pH started increasing as HCOOH from the triethylammonium formate was consumed. When the pH reached 7.4-7.45 the titration/slow addition with 12.5 M HCOOH solution in 20% DMF/EtOAc was started. The pH was maintained at pH=7.4 over 12 hrs by slowly adding the HCOOH solution. After 17 hrs the reaction mixture was clear purple, with some catalyst decomposition observed on the walls of the flask. The HPLC conversion after 17 hrs was 98%. At this point the pH of the solution was 7.8 and addition of more HCOOH solution was continued at 7.7. Further stirring up to 23 hrs led to 99% conversion. Approximately 4.7 eq. HCOOH with respect to the starting material was consumed during the reaction. After 23 hrs, the heating was stopped and the reaction mixture was stirred and allowed to cool down. The reaction mixture was concentrated, 100 mL MTBE added and the solvent removed again. 15 mL MeOH was added and the white paste refluxed for about 5 min and then 250 mL MTBE added slowly to this refluxing mixture. The resulting mixture was stirred at reflux for 30 min, cooled to RT, then to 0-5° C. and stirred for 30 min. The mixture was filtered cold and washed with cold portions of MTBE until the filtrate was colourless (8×50 mL). The resulting white precipitate was dried in the air, then under high vacuum, affording a white powder: 94% isolated yield (37.9 g); HPLC: 99.5% product, 97.8% e.e., 0.5% oxcarbazepine. The ruthenium level in the product was between 5-50 ppm.

Comparison 1a: Asymmetric Reduction with and without pH Control (Hydride Source is NEt$_3$ and HCOOH)

Reactions were carried out using a method similar to that of example 1. The substrate/catalyst ratio was 2000 and the solvent was 20% H$_2$O/EtOAc. The ligand was (S,S)-Ts-DAEN. In example 3, 1 eq. NEt$_3$ and 1 eq. HCOOH were added to the reaction mixture at the start of the reaction. Further HCOOH was added throughout the course of the reaction to maintain a pH of 7.4. In comparative example 1, 4.4 eq. Et$_3$N and 4 eq. HCOOH were pre-mixed in H$_2$O and added to the reaction mixture in EtOAc at the beginning of the reaction. Table 1 shows the results of example 3 and comparative example 1:

TABLE 1

| | Hydride source | Time (h) | Alcohol (%) | e.e (%) |
|---|---|---|---|---|
| Example 3 | 1 eq. of NEt$_3$ and 1 eq. of HCOOH added at start of reaction. Further 1.7 eq. of HCOOH added during the course of the reaction, maintaining the pH at 7.4. | 2 | 22 | 98.8 |
| | | 4 | 33 | 98.7 |
| | | 6 | 46 | 98.8 |
| | | 8 | 57 | 98.5 |
| | | 26 | 82 | 98.3 |
| | | 33 | 82 | 98.3 |
| Comparative Example 1 | Mixture of 4.4 eq. of NEt$_3$ and 4 eq. HCOOH in H$_2$O/EtOAc added at the start of the reaction. | 21 | 31 | 96.8 |

The yield of the pH controlled reaction (example 3) was much better than the yield of the reaction in which pH was not controlled (comparative example 1), despite the fact that higher quantities of hydride source reagents were used.

Comparison 1b: Asymmetric Reduction with and without pH Control (Hydride Source is [Et$_3$NH][OOCH] or [Et$_3$NH][OOCH] and HCOOH)

Reactions were carried out using a method similar to that of example 2. The substrate/catalyst ratio was 1000 and the solvent was 10% DMF/EtOAc. The ligand was Ts-DPEN rather than Ts-DAEN. 20 g of oxcarbazepine were used instead of 40 g. [Et$_3$NH][OOCH] was added to the reaction mixture at the start of the reaction and no further HCOOH was added. Table 2 shows how the results of two comparative examples using different quantities of [Et$_3$NH][OOCH]:

TABLE 2

| | [Et$_3$NH][OOCH] (eq) | Time (h) | pH | Conversion (%) | Enantiomeric excess (%) |
|---|---|---|---|---|---|
| Comparative Example 2 | 5 | 0 | 6.95 | 0 | — |
| | | 22 | 8.6 | 100 | 97.7 |
| Comparative Example 3 | 2 | 0 | 6.7 | — | — |
| | | 0.15 | 6.8 | — | — |
| | | 0.5 | 7.55 | — | — |
| | | 1.5 | 8.25 | — | — |
| | | 2 | 8.86 | — | — |
| | | 3 | 8.85 | — | — |
| | | 5 | 8.65 | — | — |
| | | 6 | 8.6 | — | — |
| | | 19 | 8.22 | 47 | 98.5 |

5 equivalents of the expensive reagent [Et$_3$NH][OOCH] provided 100% conversion after 22 hours, whereas less than 50% conversion was achieved with only 2 equivalents of the reagent. The pH of the reaction mixture increased during the course of the reaction.

The reaction was repeated on a 10 g scale using a substrate/catalyst ratio of 1500:1 and a 20% DMF/EtOAc solvent. In comparative examples 4 and 5, 5 equivalents of [Et$_3$NH][OOCH] were used and no further HCOOH was added. In example 4, only one equivalent of [Et$_3$NH][OOCH] was used but further HCOOH was added during the course of the reaction to maintain the pH at 7.4. Table 3 shows the results of comparative examples 4 and 5 and example 4:

TABLE 3

| | Ligand | Hydride Source | Time (h) | Conversion (%) | Enantiomeric Excess (%) |
|---|---|---|---|---|---|
| Comparative Example 4 | (S,S)-TsDPEN | 5 eq. [Et$_3$NH][OOCH] | 25 | 98 | 97 |
| Comparative Example 5 | (S,S)-TsDAEN | 5 eq. [Et$_3$NH][OOCH] | 20 | 97 | 96.9 |
| Example 4 | (S,S)-TsDAEN | 1 eq. [Et$_3$NH][OOCH] plus HCOOH to maintain pH 7.4 | 7 | 99 | 97.8 |

A comparison of comparative examples 4 and 5 with example 4 shows that by controlling the pH by addition of HCOOH, a much smaller quantity of the expensive reagent [Et$_3$NH][OOCH] can be used, and the reaction reaches almost complete conversion in 7 hours rather than 20-25 hours.

Comparison 2: Asymmetric Reduction using a Variety of Ligands

The activity of catalysts comprising the (S,S)-TsDAEN and (S,S)-TsDPEN ligands was compared at a 20-40 g scale. The catalysts were generated in situ by stirring [RuCl$_2$(p-cymene)]$_2$ and either (S,S)-TsDAEN or (S,S)-TsDPEN for 5-10 minutes in DMF before addition to oxcarbazepine and 1.07 equivalents of [Et$_3$NH][OOCH]. 12.5M HCOOH solution in 20% DMF/EtOAc was injected slowly at pH=7.4. The ratio of oxcarbazepine to catalyst was 3000:1. Table 4 shows the results for Examples 5 and 6 (using (S,S)-TsDAEN) and example 7 (using (S,S)-TsDPEN):

TABLE 4

| | Scale (g) | ligand | Time (h) | Conversion (%) | Enantiomeric excess (%) |
|---|---|---|---|---|---|
| Example 5 | 40 | (S,S)-TsDAEN | 23 | 99 | 98.1 |
| Example 6 | 25 | (S,S)-TsDAEN | 4 | 55 | 98.2 |
| | | | 6 | 69 | 98.3 |
| | | | 8 | 77 | 98 |
| | | | 26 | 97 | 97.9 |
| Example 7 | 20 | (S,S)-TsDPEN | 5 | 47 | 98.4 |
| | | | 6 | 54 | 98.2 |
| | | | 7 | 64 | 98.3 |
| | | | 8 | 77 | 98 |
| | | | 23 | 83 | 98 |
| | | | 26 | 85 | 97.8 |
| | | | 30 | 86 | 97.8 |

The (S,S)-TsDAEN examples show significantly better conversion than the (S,S)-TsDPEN example and show similar enantioselectivity.

Comparison 3: Asymmetric Reduction of Oxcarbazepine Using a Phase Transfer Catalyst Table 5 shows the results of three asymmetric reduction reactions wherein a phase transfer catalyst was used in addition to the ruthenium catalyst. In each reaction, the catalyst was generated in situ by adding [RuCl$_2$(p-cymene)]$_2$ and a ligand to EtOAc and stirring. (NB (R,R)-TsDTEN has the same structure as (R,R)-TsDPEN except that the phenyl groups are substituted by tolyl groups). The phase transfer catalyst was 0.1 equivalents of Bu$_4$NBr. The hydride source was 2 equivalents of [Et$_3$NH][OOCH] and additional formic acid was slowly added to the reaction mixture during the course of the reaction. The ratio of oxcarbazepine to catalyst was 2000:1 and the external reaction temperature was 110° C. The conversion in example 9, wherein the ligand was (R,R)-TsDAEN was significantly better than the conversion in examples 8 and 10, wherein the ligands were (S,S)-TsDPEN and (R,R)-DTEN.

TABLE 5

| | Ligand | Time (h) | Conversion (%) | Enantiomeric excess (%) |
|---|---|---|---|---|
| Example 8 | (S,S)-TsDPEN | 6 | 58 | 98 (S) |
| Example 9 | (R,R)-TsDAEN | 6 | 70 | 98.2 (R) |
| Example 10 | (R,R)-TsDTEN | 6 | 60 | 97.8 (R) |

Example 3

Acetylation of (S)-(+)-10,11-dihydro-10-hydroxy-5H-dibenz/b,f/azepine-5-carboxamide (S)-(+)-10,11-dihydro-10-hydroxy-5H-dibenz/b,f/azepine-5-carboxamide (500 g), obtained via asymmetric transfer hydrogenation as described above, and 4-(N,N-dimethylamino)pyridine (4 g) were suspended in dichloromethane (5.07 L). Pyridine (210 mL) was added to the suspension. The reaction mixture was heated to reflux whereupon acetic anhydride (240 mL) was added dropwise. The resulting yellowish-brown solution was stirred for 2 hours and then cooled to 30° C.

The reaction mixture was then quenched by the addition of sulphuric acid. After stirring for 10 min, the layers were separated. The organic layer was washed twice with saturated aqueous sodium bicarbonate solution and then water. Approximately half of the dichloromethane was then removed by evaporation and isopropanol (5 L) was added to the mixture which was then left to stand overnight. Further solvent was evaporated (approximately 1.5 L) and the resulting slurry was cooled to approximately 3° C. After 3 hours the solid was filtered off, washed with cold isopropanol and then dried under vacuum overnight. The dried solid was suspended in isopropanol (6.5 L) and the resulting white slurry was heated to reflux. Once a solution was obtained heating was stopped and the reaction mixture was stirred for ~1 hr at 1-5° C. Solids were isolated by filtration, washed with cold isopropanol and dried under vacuum to yield 524.2 g of white solid, 90% yield, 99.96% chemical purity, (R)-isomer below the limit of detection.

Residual ruthenium content was found to be less than 2 ppm. According to the regulatory guidelines, the oral concentration limit is 5 ppm.

Example 4

Asymmetric Reduction of Oxcarbazepine Using Higher Oxcarbazepine: Catalyst Ratio This reduction described in example 1 was carried out on oxcarbazepine (357 mmol, 90 g) using [RuCl2(p-cymene)]2 (0.066 mmol, 40.4 mg) and (S,S)-TsDAEN (0.145mmol, 61.9 mg) using four times the quantity of water. The reaction was complete in 27 hours.

Ethyl acetate was distilled from the batch while maintaining the original batch volume by the addition of water (dropwise). Temperature was maintained above 60° C. during the distillation. Approximately ⅓ into the distillation the product started to precipitate.

The mixture was cooled to 5° C., held at that temperature for one hour and then filtered. The filter cake was washed with water. The wet cake was then reslurried in ethyl acetate (350 mL) and heated to reflux for 0.5 hours. It was then cooled to 5° C. and held at that temperature for 1 hour. The mixture was then filtered and the recovered solids with ethyl acetate (120 mL). Drying under high vacuum afforded an off-white powder: 88% isolated yield (79.8 g): HPLC: 99.8% product, 98.4% e.e., 0.09% oxcarbazepine.

It will be appreciated that the invention described above may be modified.

What is claimed is:

1. A compound being (S)-(−)-10-acetoxy-10,11-dihydro-5H-dibenz/b,f/azepine-5-carboxamide and comprising about 2 ppm of ruthenium or less.

2. The compound of claim 1, having a chemical purity of (S)-(−)-10-acetoxy-10,11-dihydro-5H-dibenz/b,f/azepin-5-arboxamide of about 99.96%.

3. The compound of claim 1, comprising less than 2 ppm of ruthenium.

4. The compound of claim 1, obtained by a process comprising:
   (i) a first step comprising reducing oxcarbazepine in the presence of a catalyst and a hydride source to obtain (S)-(+)-10,11-dihydro-10-hydroxy-5H-dibenz/b,f/azepine-5-carboxamide, wherein the catalyst is prepared from a combination of [RuX$_2$(L)]$_2$ wherein X is chlorine, bromine or iodine, and L is an aryl or arylaliphatic ligand, with a ligand of formula (A) or formula (B):

(A)

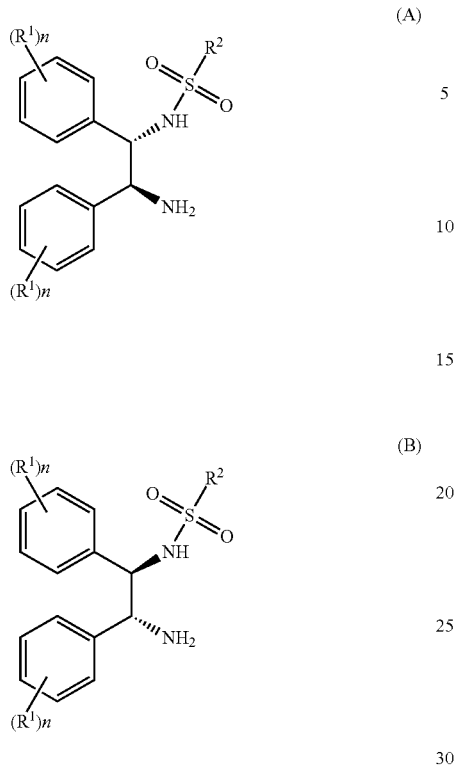

(B)

wherein $R^1$ is chosen from $C_{1-6}$ alkoxy and $C_{1-6}$ alkyl, n is a number from 0 to 5, and when n is from 2 to 5, $R^1$ is the same or different, and $R^2$ is alkyl, substituted alkyl, aryl, substituted aryl, alkaryl or substituted alkaryl;

wherein the hydride source is chosen from $NR^3R^4R^5$ and formic acid, or $[R^3R^4R^5NH][OOCH]$, or $[R^3R^4R^5NH][OOCH]$ and formic acid, or $[M][OOCH]_x$ and formic acid, wherein $R^3$, $R^4$ and $R^5$ are $C_{1-6}$ alkyl, M is an alkali metal or alkaline earth metal and x is 1 or 2, and wherein during the process a pH from 6.5 to 8 is maintained; and (ii) a second step wherein the (S)-(+)-10,11-dihydro-10-hydroxy-5H-dibenz/b,f/azepine-5-carboxamide is acylated.

5. The compound of claim 1, the (R)-isomer of (S)-(−)-10-acetoxy-10,1-dihydro-5H-dibenz/b,f/azepine-5-carboxamide being below the limit of detection.

6. The compound of claim 2, comprising less than 2 ppm of ruthenium.

7. The compound of claim 2, obtained by a process comprising:
   (i) a first step comprising reducing oxcarbazepine in the presence of a catalyst and a hydride source to obtain (S)-(+)-10,11-dihydro-10-hydroxy-5H-dibenz/b,f/azepine-5-carboxamide, wherein the catalyst is prepared from a combination of $[RuX_2(L)]_2$ wherein X is chlorine, bromine or iodine, and L is an aryl or arylaliphatic ligand, with a ligand of formula (A) or formula (B):

(A)

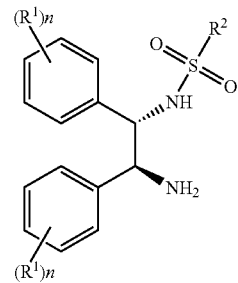

(B)

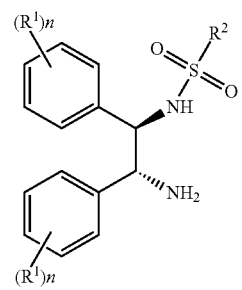

wherein $R^1$ is chosen from $C_{1-6}$ alkoxy and $C_{1-6}$ alkyl, n is a number from 0 to 5, and when n is from 2 to 5, $R^1$ is the same or different, and $R^2$ is alkyl, substituted alkyl, aryl, substituted aryl, alkaryl or substituted alkaryl;

wherein the hydride source is chosen from $NR^3R^4R^5$ and formic acid, or $[R^3R^4R^5NH][OOCH]$, or $[R^3R^4R^5NH][OOCH]$ and formic acid, or $[M][OOCH]_x$ and formic acid, wherein $R^3$, $R^4$ and $R^5$ are $C_{1-6}$ alkyl, M is an alkali metal or alkaline earth metal and x is 1 or 2, and wherein during the process a pH from 6.5 to 8 is maintained; and (ii) a second step wherein the (S)-(+)-10,11-dihydro-10-hydroxy-5H-dibenz/b,f/azepine-5-carboxamide is acylated.

8. The compound of claim 2, the (R)-isomer of (S)-(−)-10-acetoxy-10,11-dihydro-5H-dibenz/b,f/azepine-5-carboxamide being below the limit of detection.

9. The compound of claim 3, having a chemical purity of (S)-(−)-10-acetoxy-10,11-dihydro-5H-dibenz/b,f/azepine-5-carboxamide of about 99.96%.

10. The compound of claim 3, obtained by a process comprising:
   (i) a first step comprising reducing oxcarbazepine in the presence of a catalyst and a hydride source to obtain (S)-(+)-10,11-dihydro-10-hydroxy-5H-dibenz/b,f/azepine-5-carboxamide, wherein the catalyst is prepared from a combination of $[RuX_2(L)]_2$ wherein X is chlorine, bromine or iodine, and L is an aryl or arylaliphatic ligand, with a ligand of formula (A) or formula (B):

(A) 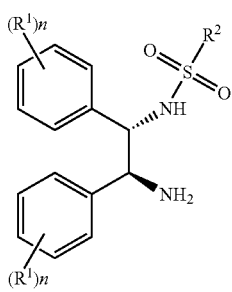

(B) 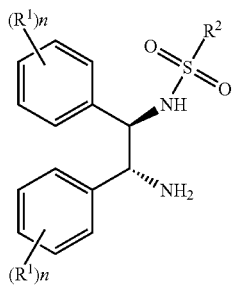

wherein $R^1$ is chosen from $C_{1-6}$ alkoxy and $C_{1-6}$ alkyl, n is a number from 0 to 5, and when n is from 2 to 5, $R^1$ is the same or different, and $R^2$ is alkyl, substituted alkyl, aryl, substituted aryl, alkaryl or substituted alkaryl;

wherein the hydride source is chosen from $NR^3R^4R^5$ and formic acid, or $[R^3R^4R^5NH][OOCH]$, or $[R^3R^4R^5NH][OOCH]$ and formic acid, or $[M][OOCH]_x$ and formic acid, wherein $R^3$, $R^4$ and $R^5$ are $C_{1-6}$ alkyl, M is an alkali metal or alkaline earth metal and x is 1 or 2, and wherein during the process a pH from 6.5 to 8 is maintained; and (ii) a second step wherein the (S)-(+)-10,11-dihydro-10-hydroxy-5H-dibenz/b,f/azepine-5-carboxamide is acylated.

11. The compound of claim 3, the (R)-isomer of (S)-(−)-10-acetoxy-10,11-dihydro-5H-dibenz/b,f/azepine-5-carboxamide being below the limit of detection.

12. The compound of claim 4, comprising less than 2 ppm of ruthenium.

13. The compound of claim 4, having a chemical purity of (S)-(−)-10-acetoxy-10,11-dihydro-5H-dibenz/b,f/azepine-5-carboxamide of about 99.96%.

14. The compound of claim 4, the (R)-isomer of (S)-(−)-10-acetoxy-10,11-dihydro-5H-dibenz/b,f/azepine-5-carboxamide being below the limit of detection.

15. A method of treating epilepsy comprising administering the compound of claim 1 to a patient in need thereof.

16. A method of treating epilepsy comprising administering the compound of claim 3 to a patient in need thereof.

17. A method of treating epilepsy comprising administering the compound of claim 3 to a patient in need thereof.

18. A method of treating epilepsy comprising administering the compound of claim 4 to a patient in need thereof.

* * * * *

UNITED STATES PATENT AND TRADEMARK OFFICE
CERTIFICATE OF CORRECTION

PATENT NO. : 9,206,135 B2  
APPLICATION NO. : 13/651844  
DATED : December 8, 2015  
INVENTOR(S) : David Alexander Learmonth, Gabriela Alexandra Grasa and Antonio Zanotti-Gerosa Page 1 of 1

It is certified that error appears in the above-identified patent and that said Letters Patent is hereby corrected as shown below:

Specification

Column 10, Lines 54-55, replace:
"(4) 10-(2-methoxybenzoloxy)-10,11-dihydro-5H-dibenz/b,f/azepine-5-carboxamide" with
--(4) 10-(2-methoxybenzoyloxy)-10,11-dihydro-5H-dibenz/b,f/azepine-5-carboxamide--.

Column 11, Lines 17-18, replace:
"(19) 10-phenylacetoxy-10,11-dihydro-5H-bibenz/b,f/azepine-5-carboxamide" with
--(19)10-phenylacetoxy-10,11-dihydro-5H-dibenz/b,f/azepine-5-carboxamide--.

Claims

Column 16, Claim 2, Line 55, replace "arboxamide" with --carboxamide--.

Column 20, Claim 16, Line 25, replace "claim 3" with --claim 2--.

Signed and Sealed this  
Twenty-ninth Day of March, 2016

Michelle K. Lee  
*Director of the United States Patent and Trademark Office*